(12) United States Patent
Darzynkiewicz et al.

(10) Patent No.: US 6,417,343 B1
(45) Date of Patent: Jul. 9, 2002

(54) PHYSICAL SEPARATION OF NUCLEIC ACIDS BY ANTIBODIES TO HALOGENATED NUCLEOTIDES

(75) Inventors: Zbigniew Darzynkiewicz, Chappaqua; Frank Traganos, New York; Gloria Juan, North Tarrytown, all of NY (US)

(73) Assignee: New York Medical College, Valhalla, NY (US)

(*) Notice: Subject to any disclaimer, the term of this patent is extended or adjusted under 35 U.S.C. 154(b) by 0 days.

(21) Appl. No.: 08/951,598

(22) Filed: Oct. 16, 1997

Related U.S. Application Data (60) Provisional application No. 60/028,806, filed on Oct. 17, 1996, and provisional application No. 60/054,392, filed on Jul. 31, 1997.

(51) Int. Cl.[7] .................... C12P 19/34; C07H 21/00; C07H 21/02
(52) U.S. Cl. ............... 536/25.3; 435/91.1; 536/25.4
(58) Field of Search ............. 435/6, 7.1, 91.1; 530/388.21, 391.1, 391.3; 935/77; 536/25.3, 25.4

(56) References Cited

U.S. PATENT DOCUMENTS

| | | | | |
|---|---|---|---|---|
| 4,711,955 A | * | 12/1987 | Ward et al. | 536/29 |
| 4,851,331 A | * | 7/1989 | Van et al. | 435/6 |
| 4,978,749 A | * | 12/1990 | Stratis et al. | 536/27 |
| 5,053,336 A | * | 10/1991 | Vanderlaan et al. | 435/240.27 |
| 5,747,258 A | * | 5/1998 | Darzynkiewicz et al. | 435/6 |

FOREIGN PATENT DOCUMENTS

| | | |
|---|---|---|
| DE | 3910151 A | 10/1990 |
| EP | 0239405 A | 9/1987 |
| WO | 9708345 A | 3/1997 |

OTHER PUBLICATIONS

Gott. et al., Biochemistry 30:6290–6295, 1991.*
Czajkowska. Human Genetics 56:185–194, 1980.*
(1) Ausubel, F.M., et al. (Eds) *Short Protocols in Molecular Biology*, 1985, pp. 4/3–4/29, John Wiley & Sons, New York.
(2) Gratzner, H.G., "Monoclonal Antibody to 5–Bromo–and 5–Iododeoxyuridine: A New Reagent for Detection of DNA Reaplication" in *Science*, vol. 218, Oct. 29, 1982, p. 474–475.
(3) Dolbeare, F., et al. "Flow cytometric measurement of total DNA content and incorporated bromodeoxyuridine" in *Proc. Natl. Acad. Sci.*, vol. 80, Sep. 1983, pp. 5573–5577.
(4) Dolbeare F. and J.R. Selden, "Immunochemical Quantitation of Bromodeoxyuridine: Application to Cell–Cycle Kinetics": in *Methods in Cell Biology*, vol. 41, 1994, pp. 297–316.
(5) Begg A.C., et al. "A Method to Measure the Duration of DNA Synthesis and the Potential Doubling Time From A Single Sample" in *Cytometry*, vol. 6, 1985, pp. 620–626.
(6) Raza A.G., et Al. "Observations regarding DNA replication sites in human cells in vivo following infusions of iododeoxyuridine and bromodeoxyuridine" in *Cell Prolif.*, vol. 24, 1991, p. 113–126.
(7) Li X., et al. "Simultaneous Analysis of DNA Replication and Apoptosis during Treatment of HL–60 Cells with Camptothecin and Hyperthermia and Mitogen Stimulation of Human Lymphocytes" in *Cancer Research*, vol. 54, Aug. 15, 1994, pp. 4289–4293.

(List continued on next page.)

*Primary Examiner*—Ardin H. Marschel
(74) *Attorney, Agent, or Firm*—Amster Rothstein and Ebenstein (57) ABSTRACT

Methods for immunocytochemical detection and isolation of RNA.

33 Claims, 7 Drawing Sheets

OTHER PUBLICATIONS (8) Li X. and Z. Darzynkiewicz "Labelling DNA strand breaks with BrdUTP. Detection of apoptosis and cell proliferation" in *Cell Prolif.* vol. 28, 1995, pp. 571–579.

(9) Jensen P.O., et al. "Flow Cytometric Measurement of RNA Synthesis Using Bromouridine Labelling and Bromodeoxyuridine Antibodies" in *Cytometry*, vol. 14, 1993, pp. 455–458.

(10) Jensen P.O., et al. "Flow Cytometric Measurement of RNA Synthesis Based on Bromouridine Labelling and Combined With Measurement of DNA Content or Cell Surface Antigen" in *Acta Oncologica*, vol. 32, No.5, 1995, pp. 521–524.

(11) Li X., et al. "The cell cycle effects and induction of apoptosis by 5–bromouridine in cell cultures of human leukaemic MOLT–4 and HL–60 cell lines and mitogen–stimulated normal lymphocytes", in *Cell Prolif.*, vol. 27, 1994, pp. 307–319.

(12) Leadon S.A., in *Nucleic Acids Research*. vol. 14, 1986, pp. 8984–8995.*

(13) Sakomoto H., et al. "5–Bromodeoxyuridine in vivo labelling of M13 DNA, and its use as a non–radioactive probe for hybridization experiments" in *Molecular and Cell Probes*, vol. 1, 1987, pp. 109–120.*

(14) Bruno S. and Z. Darzynkiewicz Cell cycle dependent expression and stability of the nuclear protein detected by Ki–67 antibody HL–60 cells: in *Cell Prolif.*, vol. 25, 1992, pp. 31–40.*

(15) Darzynkiewicz Z. "Cell Cycle analysis by Flow Cytometry" *Cell Biology: A Laboratory Handbook*, 1994, pp. 261, 271, Academic Press.*

(16) Shibui S., et al. "Double Labeling with Iodo–and Bromodeoxyuridine for Cell Kinetics Studies": in *The Journal of Histochemistry and Cytochemistry*. vol. 37. No. 7, 1989, p p. 1007–1011.*

(17) Aten J.A., et al. "Application and Detection of IdUrd and CldUrd as Two Independent Cell–Cycle markers" in *Methods in Cell Biology*, vol. 41, 1994, pp. 317–326.*

(18) Haider S.R., et al. "Immunoseparation with Immunodetection of Nucleic Acids Labled with Halogenated Nucleotides" in *Experimental Cell Research*, vol. 234, 1997, pp. 498,.*

(19) Vanderlaan M., et al. "Improved High–Affinity Monoclonal Antibody to Iododeoxyuridine" in *Cytometry*, vol. 7, 1986, pp. 499–507.*

* cited by examiner

PHYSICAL SEPARATION OF NUCLEIC ACIDS BY ANTIBODIES TO HALOGENATED NUCLEOTIDES

This application claims priority of U.S. Provisional Serial No. 60/028,806 filed Oct. 17, 1996 and U.S. Provisional Ser. No. 60/054,392 entitled Physical Separation of Nucleic Acids by Antibodies Towards Halogenated Nucleotides, filed Jul. 31, 1997.

FIELD OF THE INVENTION

The invention described below is a method for targeting nucleic acids, in particular ribonucleic acid (RNA) by incorporating into the nucleic acid a halogenated nucleic acid precursor and binding to the resulting halogenated nucleic acid an antibody to the halogenated nucleic acid precursor. This method is useful for any type of nucleic acid analysis, in particular for isolating nucleic acids, and also for labelling nucleic acids, and for separating different populations of nucleic acids. For example, this method can be used to separate deoxyriboncleic acid (DNA) from RNA and to isolate pools of nucleic acids synthesized at specific times and after specific events.

BACKGROUND OF THE INVENTION

Many methods are available for isolation and separation of nucleic acids. Most such methods are based on selective extraction of nucleic acids by organic or inorganic solvents or by specific precipitation, and do not exploit the potential of immunochemical labelling technology.

Immunological labels have been used in connection with nucleic acids in that digoxygenin or biotin -conjugated nucleotides may be used to separate out nucleic acids synthesized at the time of addition of these precursors. However, the precursors are only practical for in vitro labelling of nucleic acids already isolated from cells, since they do not easily penetrate the cell membrane. In addition, such conjugated nucleotides are expensive.

Methods for labelling DNA in vivo with halogenated precursors which are then detected by immunocytochemistry are widely used to analyze cell cycle kinetics. Detection of RNA has also been accomplished by this method. But halogenated precursors in the area of isolating and separating nucleic acids have been very little exploited. Although labelled DNA has been separated by immunoprecipitation and detected by means of antibodies immobilized on plates, no other immunocytochemical methods have been attempted with DNA. With regard to RNA, immunocytochemical separation of halogenated RNA has never been performed and it is completely unknown whether such a method could be advantageously applied to RNA.

Further, the commonly available isolation and separation methods noted above cannot differentiate between nucleic acids which are synthesized in the cell at different times, e.g. at different time intervals after induction of cell differentiation, mitogenic stimulation, carcino-genesis, drug treatment, etc. The only available approaches are analysis of transcribed DNA or nuclear runoff transcription of RNA. These methods are complex, cumbersome, and costly. Labelled nucleotides described above do not penetrate the cell membrane sufficiently well to be an alternative which provides a means of analysis readily applicable in vivo.

The inventors have solved these problems by developing a new method which exploits different aspects of these otherwise unrelated methods and provides a convenient and accessible means for isolation and separation of nucleic acids, in particular RNA, which can be used with living cells. A surprising advantage of the new method is that it permits direct separation of RNA synthesized in a given time interval from RNA which existed in the cell prior to this time interval. Such a direct method has not been available until now.

SUMMARY OF THE INVENTION

Methods for manipulating nucleic acids, in particular RNA, in a rapid, simple, and convenient manner using the tools of halogenated nucleotide precursors and antibodies capable of binding to such precursors, are the basis for this invention.

This invention provides a method for labelling RNA by incubating the RNA with a halogenated nucleotide triphosphate so as to incorporate the halogenated nucleotide triphosphate into the RNA and incubating the resulting RNA with a labelled antibody which binds specifically to the halogenated nucleotide triphosphate so as to label the RNA.

Also part of this invention is a method for isolating RNA by incubating the RNA with a halogenated nucleotide triphosphate so as to incorporate the halogenated nucleotide triphosphate into the RNA and incubating the resulting RNA with an antibody which binds specifically to the halogenated nucleotide triphosphate and which is attached to a solid support, then isolating the solid support and separating the RNA from the antibody.

The methods of this invention not only isolate RNA, but effectively separate RNA from any DNA which may be present. It is also part of this invention to separate RNA from DNA by incubating the RNA and DNA with a nucleotide triphosphate and a deoxynucleotide triphosphate, where both triphosphates are halogenated using a different halogen, differentially labelling the resulting RNA and DNA by incubating with a labelled antibody which binds specifically to the nucleotide triphosphate and a labelled antibody which binds specifically to the deoxynucleotide triphosphate, and separating the differentially labelled RNA and DNA.

Another method of this invention provides for isolating RNA synthesized during a period of time by starting to incubate the RNA with a halogenated nucleotide triphosphate at the beginning of the period of time so as to incorporate the halogenated nucleotide triphosphate into RNA, stopping the incubation at the end of the period of time, then incubating the resulting RNA with an antibody which binds specifically to the halogenated nucleotide triphosphate, and finally separating the RNA from the antibody to isolate the RNA synthesized during the period of time.

It will be apparent to the skilled person that the methods of this invention have a broad applicability both in basic research and in applied technology. The following uses for the subject methods are provided as examples:

Isolation of RNA is of interest for cloning proteins of pharmaceutical interest.

Halogen labelled nucleic acids can also be prepared in vivo by growing bacteria carrying plasmids in the presence of halogenated nucleotide precursors or in vitro by polymerase catalyzed reactions. The labelled nucleic acids can then be used as nonradioactive probes in a variety of hybridization applications and detected by routine immunochemical methods using anti-halogenated nucleotide precursor antibodies.

RNA labelled by the methods of this invention can be separated on gels and transferred to filters on which various species of RNA may be detected (since RNA bases are labelled in sufficiently high density to distinguish species), allowing for comparison of the amounts and kinds of RNA present in tumor cells versus normal cells, or before and after addition of an active agent, providing information about RNA synthetic activity.

By using pulses of halogen labelled RNA precursors as described in this invention at different times after perturbation of cells or organisms by drug treatment, radiation, signals to proliferate or differentiate, the resulting temporal sequence of events may be determined. In particular, proteins whose synthesis results from perturbation may be isolated by obtaining the corresponding RNA, and used either directly or in drug screening. Halogenated RNA precursors which are distinguished by binding to different antibodies may also be used in this way.

RNA isolated by methods of this invention may be used to determine which genes are activated as a result of drug treatment and then reverse transcribed to make complementary DNA. Such DNA may be used to obtain corresponding proteins or used directly as antisense genes to turn off gene activation if desired.

DNA may be separated from RNA by the methods of this invention, which can be used to isolate from a cell perturbed by radiation or drugs both DNA in the form of damaged genes which are being repaired and mRNA produced from genes which are not damaged and therefore are actively synthesizing proteins. From these materials, antisense genes and/or proteins can be produced for use in treatment of perturbation caused by conditions such as disease or exposure.

BRIEF DESCRIPTION OF THE DRAWINGS

Bivariate distributions showing green (FITC) and red (PI) fluorescence of HL-60 cells which were either incubated in the presence 30 $\mu$M BrdU for 1 h FIG. 1(B) or in the absence of this precursor FIG. 1(A). The cells were fixed, their DNA was denatured by exposure of the cells to 2 M HCl, and reacted with anti-BrdU MoAb which was then detected using FITC-conjugated anti-mouse IgG. DNA was counterstained with PI and the cells were analyzed by flow cytometry.

The same antibody was used to detect cellular RNA labeled with BrU FIG. 1(C, D). Towards this end, the cells were incubated with 0.5 mM of BrU for 2 h, fixed and reacted with anti-BrdU, then with FITC-conjugated anti-mouse IgG. DNA was counterstained with 7-aminoactinomycin (FIG. 11). Confirming earlier observations (11–13) the data shows that the highest rate of BrU incorporation occurs in late S phase (D). Note that RNase treatment (200 $\mu$g/ml, 30 min at 37° C.) abolishes cell labeling FIG.1(C).

The broken line indicates the level of nonspecific cell fluorescence, i.e. the mean fluorescence of the measured cell population plus three standard deviations, of the respective cells incubated with isotype IgG rather than with anti-BrdU MoAbs.

Control (unlabeled) and BrU labeled total RNA, obtained from HL-60 and U937 cells that were grown in the presence of 50 $\mu$M BrU for 20 h, was slot-blotted (8 $\mu$g/well) in duplicate onto a nitrocellulose filter by vacuum filtration. The RNA was UV cross linked, the filter was washed in SSC and then TBST and then subjected to immunoblot analysis using anti-BrdU MoAb. The binding of the antibody was detected by enhanced chemiluminescence (ECL) using peroxidase labeled anti-mouse IgG secondary antibody provided with the ECL kit. (A) Immunodetection was done in the absence of uridine for equal amounts of RNA from two cell lines. (B) Serial dilutions of RNA (8, 4, and 2 $\mu$g per well) in duplicate was immunodetected in the presence of 0.3 M uridine as a blocking agent. The blots containing control, unlabeled RNA are indicated by minus symbol while those containing BrU-labeled RNA by plus.

The cultures of DH5a cells containing $p21^{WAF1}$ or $p57^{KIP2}$ plasmids were grown in the presence of 50 $\mu$M BrdU. Plasmids were isolated and digested with the appropriate restriction enzymes (See Material and Methods). (A) The products were seperated on EB agarose gel (B); DNA from the gel was transfered to a nitrocellulose membrane by routine Southern transfer and BrdU incorporated into plasmid DNA was immunodetected as described in FIG. 2.

Unlabeled (A,B,E) or BrdU-labeled (B,D,F) plasmid DNA (5 $\mu$g/sample) was boiled and added to the antibody coated sepharose or magnetic beads and incubated for 1 hr. The beads were rinsed and a sample from each reaction was observed by microscopy. Binding of DNA to anti-BrdU MoAb coated sepharose beads was revealed by staining the beads with PI and observing them by fluorescence microscopy (B and D). To visualize the beads themselves the same specimen was viewed under interference contrast (A and C). The presence of red fluorescence halo (arrows) of the PI stainable material indicates attachment of BrdU-labeled DNA to the beads (D). Likewise, aggregation of magnetic beads (F) indicates attachment of BrdU-labeled DNA chains to their surfaces.

(A) Parallel cultures of each cell line were grown for 4 hr in the presence 50 $\mu$M BrUrd. To one flask of culture, 0.1 $\mu$M PMA was added to induce IL1 gene transcription. Total RNA was extracted from all four cultures and immunoprecipitated with magnetic beads coated with anti-BrdU MoAb. After washing the beads in PBS-0.1%BSA, the bead-bound mRNA was released by heating the complexes at 80° C. for 10 min. The beads were sedimented and the supernatant was subjected to RT-PCR using IL1 primers. The products were separated on a 1.5% EB agarose gel containing 5 $\mu$g/ml EB. A PCR reaction with 1 $\mu$g of total HL-60 RNA (second lane) and a reaction without an RNA template (third lane) were used as positive and negative controls respectively. Control RNA provided with the kit was also used as a positive control for the PCR reaction (external right lane).

(B) Equal amounts of RNA from PMA induced and un-induced HL-60 cells growing in the presence of BrU (as in panel A) were incubated with either uncoated (anti-BrdU−) or coated with anti-BrdU MoAb (anti-BrdU+) magnetic beads. RNA was recovered from the beads and used in the RT-PCR reaction. The positive controls as described in panel A were also used here. The products were separated on an EB containing gel. Note the presence of a strong 0.4 kbp band in the PMA induced cells after RNA separation with anti-BrdU coated beads. Left lanes are MW standard lanes.

the bands from top to bottom represent 1.3, 1.1, 0.9, 0.6 and 0.3 kbp standards.

(A) An EB-agarose gel of the product of RT-PCR that was carried out with 1 μg of the control RNA per reaction (as described in FIG. 5), except in lane 2 where RNA was omitted as a negative control. Lane 3 contains a normal PCR mix with 300 μM dTTP while lane 4 contains a mixture of dTTP and BrdUTP at 150 μM each and lanes 5–8 contain 30, 100, 200 and 400 μM BrdUTP (without dTTP), respectively. After 40 cycles, the products are seen in the lanes with 300 μM dTTP, in the mixture of dTTP and BrdUTP, and at >100 μM concentrations of BrdUTP. (B) DNA from the gel was transferred to a blot and immunodetected as described in FIG. 3. (C) An agarose gel of the products of RT-PCR using different quantities of RNA, from 1000 to 1 ng (lanes 1–8, respectively) per RT-PCR reaction, to test the sensitivity of the reaction, utilizing 300 μM BrdUTP (as described in FIG. 5). (D) DNA was transfered onto filters and immunodetected using anti-BrdU MoAbs and ECL, as described in FIG. 3. (E) Immunoblots (Southern/Western) of products of the random primer polymerase reaction using mouse glyceraldehyde 3-phosphate dehydrogenase (G3PDH), human G3PDH and p21$^{WAF1}$ cDNAs as templates. In one set of reactions, with each template dTTP was replaced by BrdUTP. The products were seperated on a gel, transferred to nitrocellulose filters and immunodetected utilizing anti-BrdU and ECL. As expected, only BrdU labeled products are detected.

DETAILED DESCRIPTION OF THE INVENTION

The methods of this invention are drawn to labelling and isolating nucleic acids, in particular RNA. A skilled person will appreciate that although the following discussion focusses primarily on RNA, the same techniques can be readily used with any type of DNA to obtain the same ends. RNA is intended to include mRNA as produced by procaryotic or eucaryotic cells or as synthetically produced by known methods, other types of RNA produced in cells including transfer RNA (tRNA) and ribosomal RNA (rRNA).

The methods of this invention employ tools with which nucleic acids such as RNA may be targeted and isolated. The following discussion is meant to clarify the operation of the invention, but not to limit the invention to any particular mechanism or technique. In its basic aspect, the invention employs as a tool a nucleotide precursor (e.g. a nucleotide triphosphate) which when added to a medium containing RNA (e.g. a cell culture) is incorporated into the RNA since it is a standard chemical building block. However, this precursor is distinguished from its natural counterparts by halogenation—which makes it possible to keep track of the RNA which has taken up the precursor into its structure ("halogenated" RNA). A very effective means of keeping track of the "halogenated" RNA is by using a second tool, antibodies designed to bind specifically to the halogenated nucleotide precursors. These antibodies are capable of "seeing" the precursor even after it has been incorporated into an RNA. When labelled, the antibodies will bind to the halogenated RNA, thus labelling the RNA. When attached to a solid support, the antibodies will bind the RNA and sequester it. It is also possible to differentially label DNA and RNA using precursors and antibodies. In addition, by adding precursor at a specific time point and then controlling the length of the incubation, it is possible to obtain RNA synthesized within a selected window of time.

Thus the methods of this invention include a method for labelling RNA by incubating the RNA with a labelled nucleotide precursor such as a halogenated nucleotide triphosphate and exposing the resulting "halogenated" RNA to a labelled anti-halogenated nucleotide triphosphate antibody to label the RNA. The labelled RNA may then easily be detected in order, for example, to determine that RNA is being synthesized. RNA may also be isolated by sequestering the labelled RNA. Another method of isolating RNA involves exposing the "halogenated" RNA to an anti-halogenated nucleotide triphosphate antibody (which may or may not be labelled) which is bound to a solid support, thus sequestering the RNA to the support. The RNA is separated from the antibody to isolate the RNA in both instances.

RNA and DNA may be separated from each other by incubating the nucleic acids with nucleotide precursors specific for each one, for example a nucleotide triphosphate which is incorporated into RNA and a deoxynucleotide triphosphate which is incorporated into DNA. The two precursors are distinguished by each having a different label, for example being labelled with different halogens. Thus one could add brominated uridine triphosphate and iodinated deoxyguanine triphosphate. The former would be incorporated into RNA and the latter into DNA. The RNA and DNA are then separated by using differentially labelled antibodies, one of which is specific for the brominated uridine triphosphate and the other of which is specific for the iodinated deoxyguanine triphosphate. The resulting differentially labelled nucleic acids may then be easily separated by means known to a skilled person.

Another method of this invention provides an efficient means for isolating RNA synthesized during a period of time. The nucleotide precursor is added to the RNA at the beginning of a period of time, and allowed to incorporate until the end of the time period. Since only RNA which is in the process of being synthesized will incorporate the nucleotide precursor, the RNA which contains the precursor is RNA which has been synthesized during that period of time. RNA synthesized before the time period will not contain precursor, nor will RNA synthesized after the time period (since the amount of precursor used is known, then the amount remaining after the end of the time period may be calculated by the skilled person so that the small amount of RNA which incorporates precursor after the end of the time period may be accounted for and disregarded, alternatively a quantity of precursor that would be fully incorporated by the end of the time period may be used). After the end of the time period, the "halogenated" RNA is exposed to the corresponding antibody as described above, either labelled and/or bound to a solid support, and thus detected and/or isolated. For example the RNA may be extracted from cells by known methods and immunoprecipitated for isolation. Techniques such as PCR may be exploited to further analyze the isolated RNA.

The methods of this invention require obtaining media which contain RNA, and optionally DNA. Such media may contain living cells (prokaryotic or eukaryotic) in culture, or viruses, or may be other media in which nucleic acids are present and are being synthesized, including multicellular organisms. In particular, cells which have been stimulated to divide, or to produce particular proteins are media to which the methods of this invention may be fruitfully applied. For example a cell culture may be exposed to a candidate drug compound and then analyzed by the methods of this invention to determine whether RNA synthesis has been stimulated by the compound (by detecting labelled RNA), what particular RNA and how much of it have been made (by isolating, then sequencing or expressing the RNA), and even the time-course of RNA synthesis (by adding halogenated nucleotide triphosphate at fixed time periods after stimulation, and allowing the incubation to continue for set time periods). A skilled practitioner will be aware of various contexts in which the methods of this invention can be applied, and will be readily able to design and carry out experiments based on the information provided herein.

The methods of this invention may also be applied to "nonliving" media such as cell-free solutions and fixed cells, however the necessary enzymes for catalyzing nucleic acid synthesis need also be added as discussed below.

As a skilled person will realize, these methods require use of various standard techniques and materials to provide appropriate conditions for such details as incorporating a nucleotide precursor into a target nucleic acid, binding an appropriate antibody to the incorporated precursor, purifying RNA to which an antibody on a solid support has bound, extracting nucleic acids from media such as cell culture for analysis, blotting onto nitrocellulose filters, and the like. These techniques are well known to a skilled person, and the materials required are readily obtainable. A skilled person will be able to perform these techniques, and also vary and "tweak" conditions to provide the most suitable conditions and results for any particular application of the methods herein. For example the well-known techniques of Northern, Southern, and Western blots may be used for analysis of nucleic acids labelled by the subject methods.

The nucleotide precursors of this invention include any compound which can be incorporated into the structure of RNA in cell culture and can be labelled. In particular, halogenated nucleotide triphosphates are contemplated. Specific nucleotide triphosphates include uridine triphosphate, adenosine triphosphate, cytosine triphosphate, and guanine triphosphate. Also useful in this invention are deoxynucleotide precursors which are incorporated into DNA, such as halogenated deoxynucleotide triphosphates, including deoxyuridine triphosphate, deoxythymidine triphosphate, deoxyadenine triphosphate, deoxycytosine triphosphate, and deoxyguanine triphosphate.

Uridine triphosphate and deoxyuridine triphosphate are preferred, however any triphosphate may be used. A preferred halogen is bromine, however chlorine, fluorine, and iodine are also useful in this invention. Brominated uridine (BrU) and brominated deoxyuridine (BrdU) are particularly preferred.

The structure of nucleotide precursors, in particular nucleotide and deoxynucleotide triphosphates, are very well known, both in unmodified form, and as modified by the addition of a halogen atom. Nucleotide precursors are readily available from commercial supply houses, or may be synthesized by known routes or isolated from cells by known methods. Halogenated nucleotide precursors are also readily available commercially (for example from Sigma Chemical Co., St. Louis Mo.; Calbiochem, La Jolla Calif.; and Aldrich Chemical Co., Milwaukee Wis.) or may be produced by a skilled person by known techniques.

Antibodies used in this invention are capable of binding specifically and with acceptable affinity to halogenated nucleotide precursors, in particular to halogenated nucleotide triphosphates. The particular antibody used is selected to bind specifically to the particular halogenated nucleotide precursor used in any particular method. For example, when BrU is used the corresponding antibody used is anti-BrU. Antibodies specific for selected halogenated nucleotide triphosphates are commercially available (for example from Coulter Corp., Miami Fla.; Boehringer Mannheim, Indianapolis Iowa; and Becton-Dickinson, San Jose Calif.).

In addition, such antibodies can be obtained by techniques well known to the skilled person. For example, polyclonal antibodies to a given halogenated nucleotide precursor may be obtained by immunizing an animal such as a mouse by injecting the precursor as an antigen, then isolating polyclonal serum from the body fluids (e.g. ascites) and testing its activity against the antigen by known assays. In addition monoclonal antibodies may be obtained by known techniques, for example by obtaining clonal B cells from the immunized animal, fusing them with immortal immune cells to form hybridomas, then testing the activity of the hybridoma supernatants by known techniques to obtain a hybridoma which secretes the desired monoclonal antibody.

It is not necessary to label the antibody for all methods of this invention, however in general labelled antibodies are very useful in this invention. Labelling of antibodies is well known to the skilled person. Any label may be effectively used in this invention, and many such labels will be familiar to the skilled persons. Examples of labels include flourochrome labels such as fluorescein isothiocyanate and phycoerythrin (visualized by fluorescence), peroxidase labels, digoxigenin labels, and biotin labels (radiolabels may be used but are less convenient due to expense and disposal issues). A skilled person will be well able to determine qualitative information (for example localizing materials within cells) and quantitative information (for example in the well-known technique of fluorescence-activated cell sorting) from analysis of labelled RNA, and will also be able to immunoisolate RNA based on the labelling (for examples of techniques see the Materials and Methods section below). Indirect or sandwich labelling may be provided by using a labelled antibody to the anti-nucleotide precursor antibody. Preferred labels are fluorescein and peroxidase.

Antibodies bound to a solid support are a useful tool in this invention. Any solid support familiar to the skilled person is contemplated in this invention. Examples of solid supports include solid particles, plates, microspheres, beads, magnetized microspheres, and fibers. In particular, beads such as magnetic beads and Sepharose beads are preferred. Such supports are readily available from numerous biological supply houses. Techniques for coupling antibodies to solid supports are well known to the skilled person.

If the medium for analysis does not contain living cells or other entities capable of synthesizing nucleic acids, then it is necessary to add enzymes which catalyze the addition of nucleotide precursors to RNA (or deoxynucleotide precursors to DNA) according to the methods of this invention. Such enzymes are well known to the skilled person and are readily obtainable (for example from Sigma Chemical Co., St. Louis Mo.; and Boehringer Mannheim, Indianapolis Iowa). Particular enzymes include reverse transcriptase, terminal deoxynucleotidyl transferase, and DNA polymerase.

EXAMPLES

The Examples which follow are provided to illustrate the present invention but are not intended to limit the invention in any way. A skilled person will readily appreciate that there are a variety of other embodiments which are well within the scope of the present invention. The Examples are divided into a section describing the materials and methods employed, and a section describing the results.

Materials and Methods

Cells: Human promyelocytic leukemic HL-60 cells and human histiocytic lymphoma U937 cells were purchased from the American Type Culture Collection, (Rockville, Md.). The cells were cultured in RPMI 1640 medium supplemented with 10% fetal bovine serum, 100 units/ml of penicillin, 100 µg/ml of streptomycin and 2 mM L-glutamine (all from GIBCO BRL, Grand Island, N.Y.), as described (6,10). To ensure exponential asynchronous growth, the cells were split every third day so that their density did not exceed $5 \times 10^5$ cells/ml. The cultures were periodically tested for mycoplasma infection by staining of cytocentrifuge preparations with 4,6-diamidino-2-phenylindole (DAPI; Molecular Probes, Inc., Eugene, Oreg.). Other details concerning culture conditions are described in earlier publications (9,10,17). To induce expression of the interleukin 1 (IL1) gene, two flasks of exponentially growing cultures of either HL-60 or U937 cells were incubated for 4 h with 50 µM BrU and then into one flask of each cell type 100 nM PMA (Sigma) was administered. At the end of incubation the cells were lysed and total RNA was isolated by RNAzol B(Tel-Test, Friendswood, Tex.) method.

Incorporation of BrU into RNA or BrdU into DNA and immunocytochemical detection of the incorporated precursors: To label cellular RNA or DNA, BrU or BrdU (both from Sigma Chemical Co., St. Louis, Mo.) was added into the culture media at a concentration and for a period of time as specified in the Results section or in the Brief Description of the Drawings. Incubation of cells with the halogenated DNA or RNA precursors and the subsequent steps in the procedure were carried out in the dark, using aluminum foil wrapped flasks or tubes. Following incubation with BrU or BrdU, the cells were fixed in suspension in 70% ethanol at 4° C. for at least 4 h. The cells were then centrifuged (300×g, 5 min), resuspended in phosphate buffered saline (PBS) and centrifuged again. The cell pellet consisting of approximately $10^6$ cells was then resuspended in 100 µl of PBS containing 0.5 µg of anti-BrdU MoAb (Phoenix Flow Systems, San Diego, Calif.) and incubated at 37° C. for 1 h, or at 4° C. overnight. In the case of cells which were preincubated with BrdU, to make the precursor incorporated into DNA accessible to the antibody, the cells were pretreated with 2 M HCl to denature DNA, as described (6,18). In the second step of the reaction, the cells were centrifuged again (300×g, 5 min), the pellet was suspended in 100 µl of PBS containing 0.5 µg of the FITC-conjugated goat anti-mouse antibody (Sigma) to BrdU and incubated at 37° C. for 1 h. After counterstaining cellular DNA with 10 µg/ml of propidium iodide (PI; Molecular Probes, Inc., Eugene, Oreg.), cellular fluorescence was measured by flow cytometry as described (18).

Figure 1A:
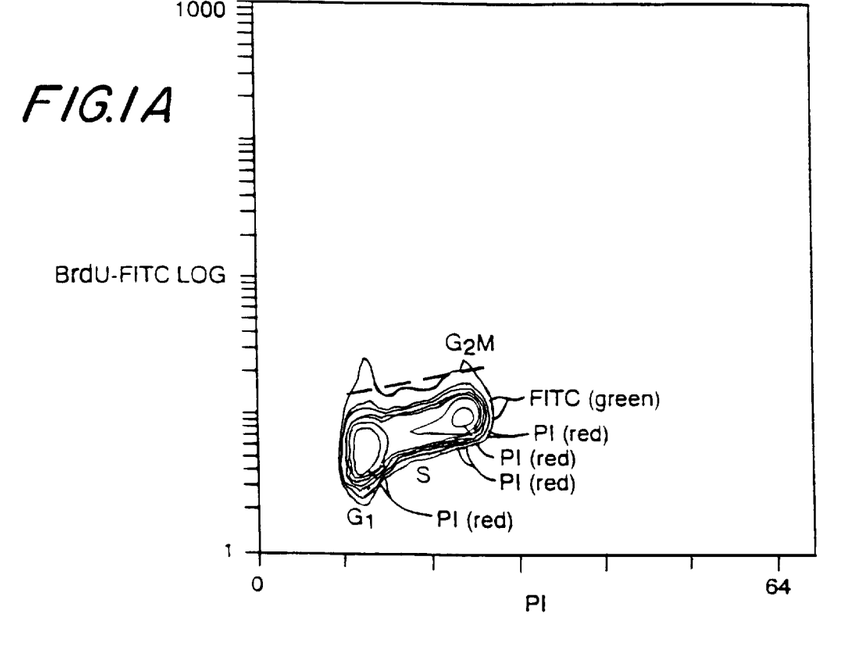
FIGS. 1A–D. The specificity of immunocytochemical detection of BrdU-labeled DNA and BrU-labeled RNA with anti-BrdU MoAb used in the present study.
Figure 1B:
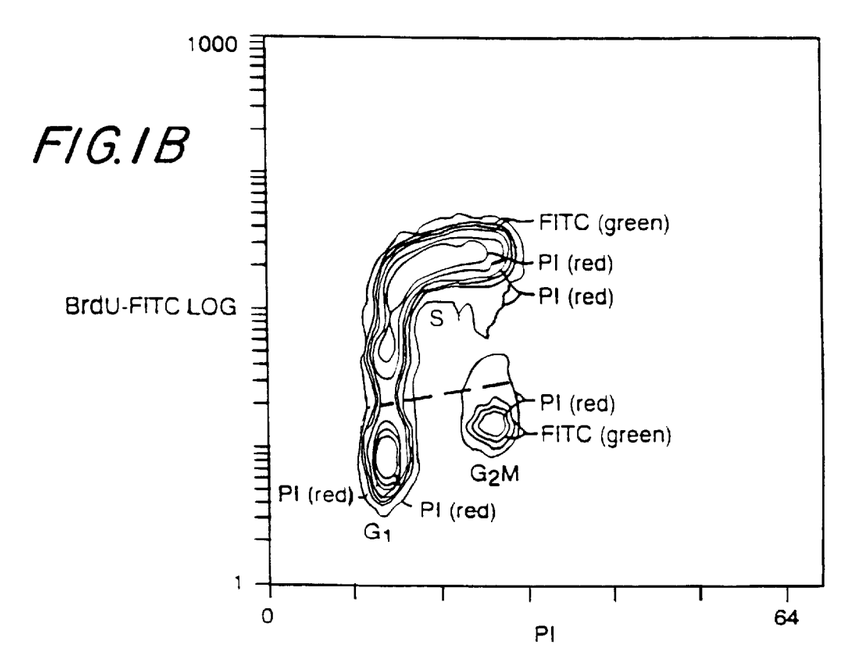
Figure 1C:
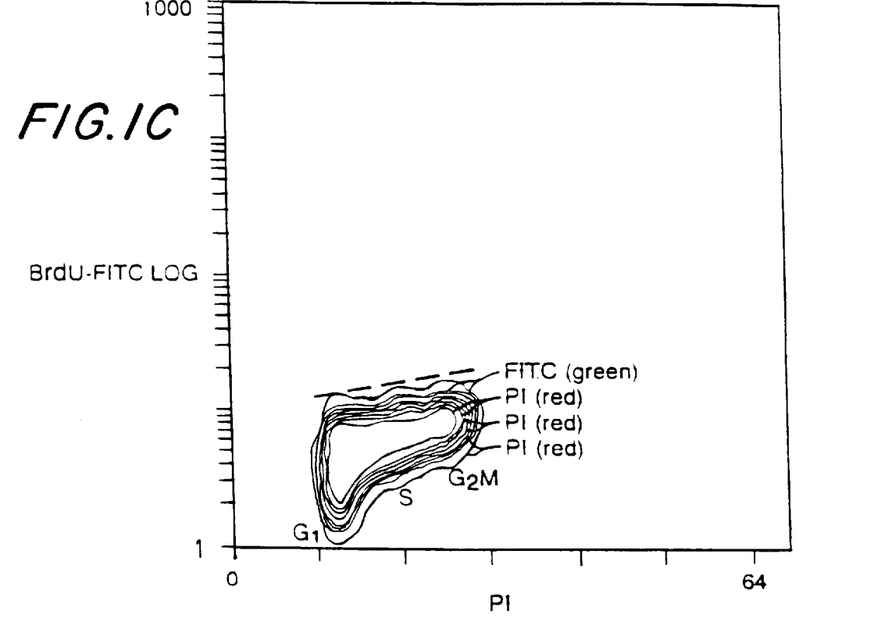
Figure 1D:
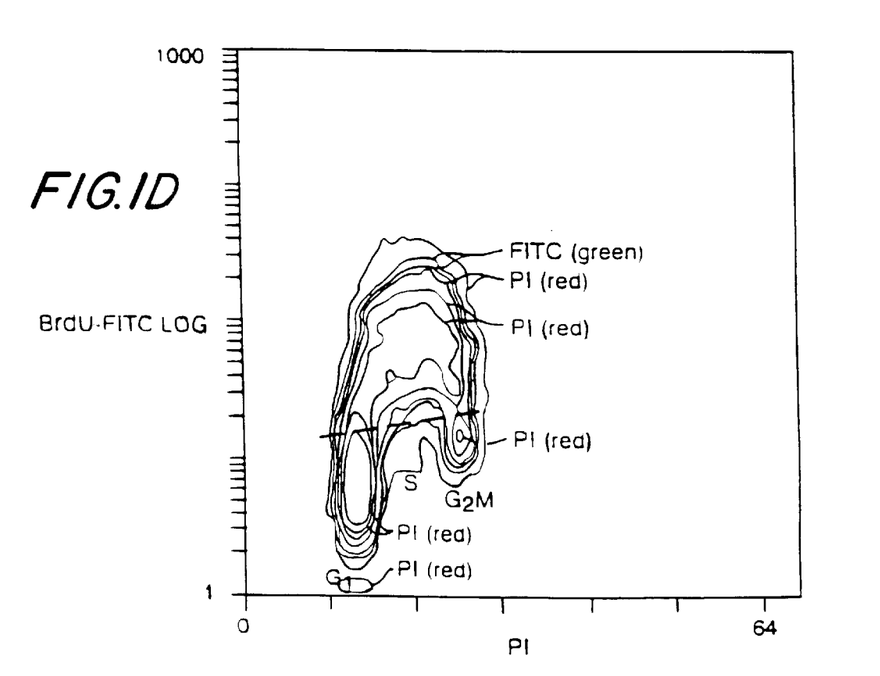
Figure 2A:
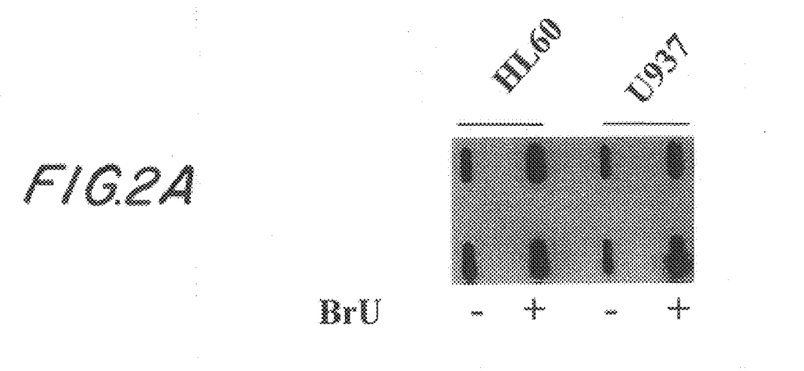
FIG. 2. Northern/Western detection of BrU labeled RNA.
Figure 2B:
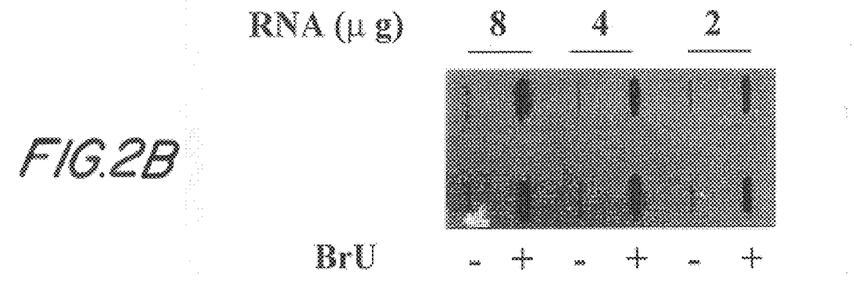

Northern/Western analysis of nascent RNA: The RNA precursor BrU was added to cultures of exponentially growing HL-60 and U937 cells at a final concentration of 50 mM for 20 hrs. The cells were collected by centrifugation and total cellular RNA was prepared by the RNAzol B (Tel-Test) method as per the manufacturer's instructions. Eight µg of the labeled or unlabeled RNA from each cell line was slot blotted in duplicate wells onto a nitrocellulose membrane using a vacuum manifold (GIBCO BRL). The blot was cross linked in the Stratalinker (Stratagene, La. Jolla, Calif.), washed in 6×SSC, and in TBST (10 mM Tris HCl, pH 8.0; 150 mM NaCl; 0.05% Tween 20), blocked in 5% milk, and incubated with a 1:200 dilution of the anti-BrdU antibody (Phoenix Flow Systems) in TBST-1% milk for 1 hr at room temperature. The blot was then washed three times with TBST and 1:2000 dilution of the second antibody (peroxidase labelled anti-mouse IgG) was added for 1 hr, followed by three washes, and detection by enhanced chemiluminescence (ECL, Amersham Life Science, Arlington, Ill.) (FIG. 2A). To block non-specific binding of the antibody to unlabeled RNA uridine (Sigma) at a final concentration 0.3 M was included to the TBST buffer during immunodetection (FIG. 2B).

Figure 3A:
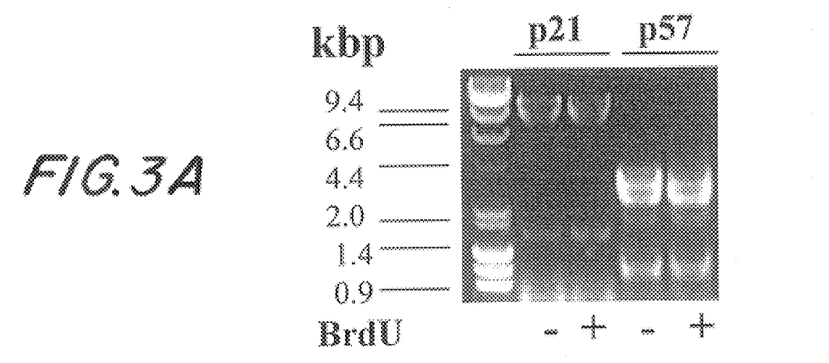
FIG. 3. Southern/Western detection of BrdU-labeled DNA.

Southern/Western detection of incorporated BrdU into plasmid DNA: Two cultures of each cell (DH5a) transformed with vectors for CDK inhibitors p21$^{WAF1}$ or p57$^{KIP2}$ were grown overnight, one in the absence, another in the presence of 50 µM BrdU. The plasmid preparations were made by the miniprep method using alkaline lysis (2). Five µg of each plasmid (labeled or unlabeled with BrdU) was digested with the appropriate restriction enzymes (Not1 for p21 and EcoR1/Hind III for p57). Restriction enzyme digestion was stopped with 0.5 M EDTA, and the products were separated on a 1% EB (ethidium bromide), agarose gel (FIG. 3A). DNAs in the gel were transferred onto a nitrocellulose membrane by Southern transfer (2). The membrane was cross linked in the UV Stratalinker (Stratagene), washed with 2×SSC and then in TBST and immunoblotted as described above with anti-BrdUrd antibody (FIG. 3B).

Immunoprecipitation of BrU labeled DNA and RNA

Preparation of anti-BrDU MoAb-coated magnetic beads: For separation of each sample of nucleic acid, 50 µl aliquots of goat anti-mouse IgG-coated magnetic beads (Dynal, Lake Success, N.Y.) were washed 3 times in PBS containing 0.1% bovine serum albumin (BSA). The final bead pellet was resuspended in 0.2 ml of 0.1% BSA in PBS. Anti-BrdU MoAb (Phoenix Flow Systems, 2.5 µg in 2.5 µl) was added to the suspension and the mixture was incubated at room temperature for 1 hr with shaking. The pellets were then washed three times with 0.1% BSA in PBS and resuspended in 0.2 ml of this solution. Preparation of anti-BrdU MoAb-coated protein A sepharose beads: Protein A sepharose beads (Pharmacia, Uppsala, Sweden) were rehydrated as per manufacturers instructions. The slurry (50 µl per sample) was washed 3 times in dilution buffer (0.1% BSA and 0.01% sodium azide in PBS). The final pellet was resuspended in 0.2 ml of this buffer and 2.5 µg of the anti-BrdU antibody was added per sample. The mixture was incubated at room temperature for 1 hr with gentle rocking, the beads were washed three times and resuspended in 0.2 ml of the dilution buffer.

Immunoprecipitation of the labeled nucleic acids: BrU labeled and control, unlabeled nucleic acids (5 µg each) prepared as described above, were denatured by boiling (DNA) or heating at 80° C. (RNA) for 10 min, and added to the coated beads. The mixtures were incubated at room temperature for 1 hr with gentle shaking, after which the beads were washed twice, resuspended in 0.2 ml of dilution buffer and observed under the microscope for agglutination with unlabeled or labeled DNA. The presence of DNA on the sepharose beads was detected by staining 20 µl of each suspension with propidium iodide (PI, Molecular Probes); the red fluorescence of the dye bound to DNA was observed by fluorescence microscopy under blue light illumination. During RNA precipitation, 0.3 M uridine was included as a blocking agent. All the solutions were made in DEPC treated water.

Figure 5A:
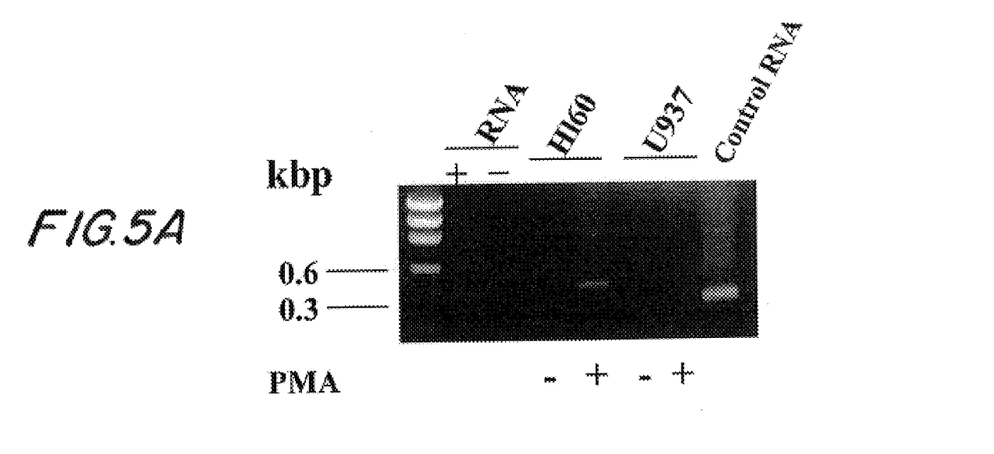
FIG. 5: Immuno-separation of BrU labeled IL1 mRNA from HL-60 and U937 cells.
Figure 5B:
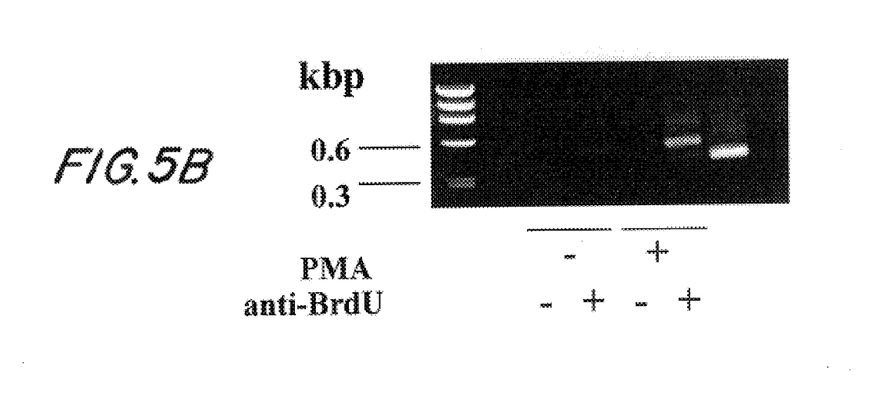

Recovery of mRNA after immunoprecipitation: Two cultures of HL-60 and U937 cells were grown in the presence of 50 µM BrU for 4 h. To induce the expression of the IL1 gene, 100 nM PMA was added to the experimental culture. RNA was isolated and immunoprecipitated with anti-BrdU MoAb- bound magnetic beads as described earlier. The bead-RNA complexes were rinsed twice with dilution buffer, each time the beads were magnetically sedimented, the final supernatant was completely removed, and the pellet was resuspended in 10 μl of water and heated at 80° C. for 10 min. The beads were sedimented again and 5 μl of this supernatant was used in the RNA PCR reaction as per protocol of the EZ Tth RNA PCR kit including the IL1 primers (Perkin Elmer, Norwalk, Conn.). The control RNA from the kit and HL-60 RNA were used as a positive control and a reaction without RNA was used as a negative control in the PCR reaction. The products were resolved on EB agarose gels. To account for any non-specific binding of RNA to the beads this experiment was repeated with antibody coated and uncoated beads, using control or induced HL-60 RNA as well as the positive and the negative controls described above. The PCR products were separated on ethidium bromide (EB)- agarose gel (FIG. 5B).

Figure 6A:
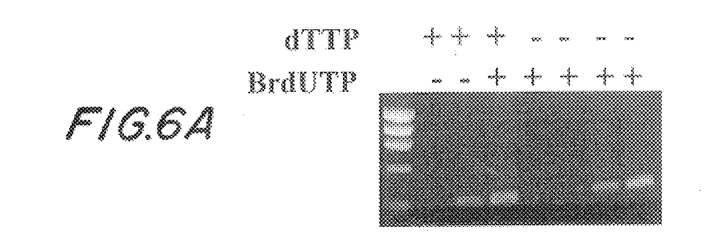
FIG. 6: Immunoblotting and immunodetection of in vitro synthesized DNA.
Figure 6B:
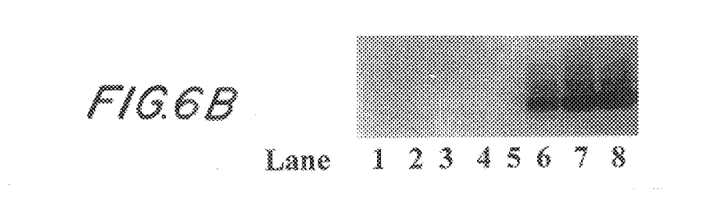
Figure 6C:
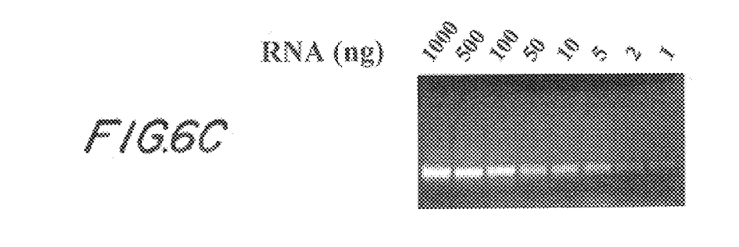
Figure 6D:
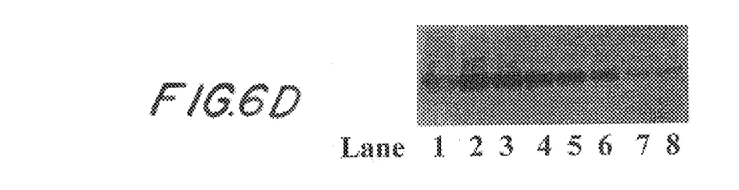

Incorporation of BrdUTP in PCR product: In a series of experiments, the incorporation of BrdUTP into PCR product and subsequent detection of the product with anti-BrdUrd antibody was optimized. Control RNA (1 μg) from the kit was reverse transcribed and PCR amplified (Perkin Elmer, EZ RNA PCR kit). Reactions were run so that all the components of the kit were used as directed, or in which dTTP was partially, or totally replaced with different concentrations of BrdUTP. The products were separated on a 1.5% EB agarose gel and the DNAs were then transferred to a nitrocellulose membrane by routine Southern transfer. The membrane was stained with anti-BrdU antibody and the binding of the antibody was detected by the ECL method as described earlier in this section (FIG. 6A and 6B). Next, a titration of the template RNA (ranging from 1 μg to 1 ng) was performed in a PCR reaction in which a sub-maximum number of PCR cycles (35 instead of 40) were carried out. The DNA from the gel was transferred to nitrocellulose by routine Southern transfer. The blot was stained with the antibody and detected by the ECL method (FIG. 6C and 6D).

Figure 6E:
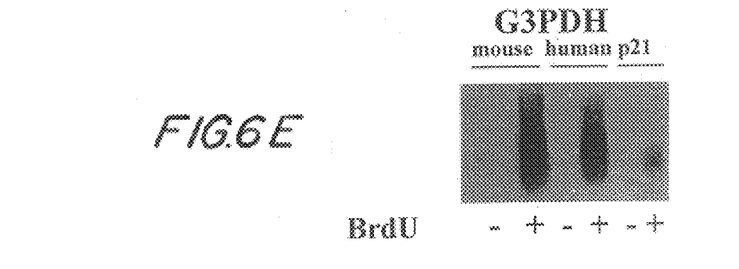

Incorporation of BrdUTP in random primer labeling of DNA: Three different cDNAs were synthesized by random primer reactions using the Klenow polymerase. For each cDNA, two reactions were set up one using dTTP in one (normal) while in the other dTTP was replaced by BrdUTP. The reactions were carried out at 37° C. for 2 hr, the products were separated on 1.5% agarose gel, transferred onto a nitrocellulose membrane by Southern transfer, stained with the antibody and detected by the ECL method (FIG. 6E).

Results

Specificity of the anti-BrdU MoAb towards BrU or BrdU labeled RNA or DNA: FIG. 1 illustrates immunocytochemical detection of BrdU-labeled DNA or BrU-labeled RNA with the anti-BrdU MoAb. In the case of cells preincubated with BrdU to make the precursor incorporated into DNA accessible to the antibody, the cells had to be pretreated with HCl to denature DNA (6,18). No denaturation step was required to make BrU incorporated into RNA accessible to the antibody (11,13). Subsequent cell incubation with FITC-conjugated anti-mouse IgG revealed the presence of the intracellularly bound anti-BrdU MoAb. After counterstaining cellular DNA with PI cellular fluorescence was measured by flow cytometry. As it is evident (FIG. 1A), the anti-BrdU MoAb specifically detected newly synthesized DNA, because S phase cells, i.e. the cells with DNA content between a DNA index (DI) of 1.0 and 2.0, were FITC-labeled after 1 h pulse of BrdU. This antibody also cross-reacted with RNA which contained incorporated BrU, because it labeled the cells which were preincubated with BrU. The detection of the incorporated BrdU or BrU was abolished after cells preincubation with DNase or RNase, respectively (FIG. 1).

Immunodetection of filter bound, BrU or BrdU labeled nucleic acids: Incorporation of BrU into nascent ribosomal RNA or BrdU into plasmid DNA was detected by the "Northern/Western" or "Southern/Western" methods respectively. Namely, the nitrocellulose filter bound labeled nucleic acids were detected by Western blotting using anti-BrdU antibody and the ECL detection system (FIGS. 2 and 3).

FIG. 2A however shows that the antibody cross-reacted with unlabeled RNA. This suggested that the antibody (originally developed against BrdU) also recognized uridine present in RNA molecules as an epitope. To suppress interactions of the antibody with endogenous uridine and thereby enhance its specificity to the brominated nucleotide, 0.3 M free uridine was included during incubation with the primary antibody. This resolved the problem of non-specific binding, since the presence of uridine during the immuno-detection steps significantly reduced the non-specific binding of the antibody to unlabeled RNA (FIG. 2B). The reduction was confirmed by densitometric analyses of the films, which showed that the intensity of the non-labeled bands (background, RNA extracted from unlabeled cells) decreased by about four fold in the presence of free uridine, without affecting the intensity of the BrU labeled bands.

Figure 3B:
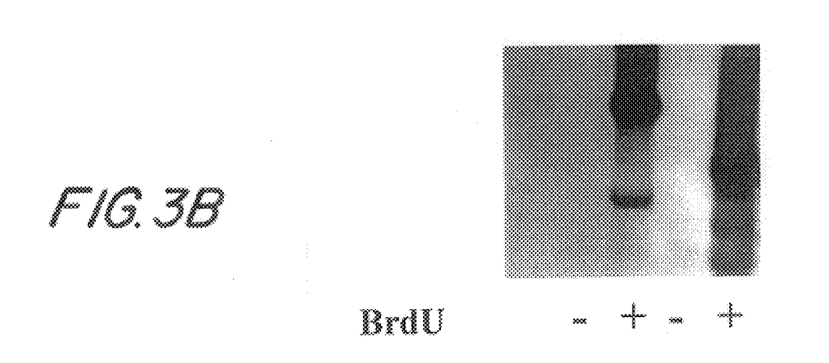

It was also observed during these experiments that neither BrU nor BrdU had any apparent adverse effects on the growth kinetics of the cells tested here. The bacterial cells grow normally, in the presence of BrdU, the quantity and the quality of the plasmid DNA harvested from the cells that incorporated BrdUrd was not different from the control cells, since both the labeled and the unlabeled plasmids produced similar products during the restriction digestion (FIG. 3A). However, only the labeled nucleic acids stained with the antibody in the Western analysis (FIG. 3B).

Immunoprecipitation of bromine labeled nucleic acids with anti-BrdU MoAb coated beads: After showing that nascent nucleic acids can be labeled and detected by immunochemical methods, the next set of experiments were designed to test whether bromine labeled nucleic acids that are extracted from live cells would bind to BrdU antibody coated solid particles. Either sepharose or magnetic beads were coated with anti-BrdU antibody and mixed with halogenated nucleotide-labeled or unlabeled nucleic acids (FIG. 4). Note the presence of a red fluorescence halo (arrows) of the PI stainable material around the beads incubated with DNA isolated from plasmids growing in the presence of BrdU (D) and lack of it after incubation with the unlabeled plasmid DNA (B). Likewise, the red halo was present after incubation of the beads with rRNA isolated from cells growing in the presence or absence of BrU for 24 h. However, when the beads were incubated with rRNA in the presence of 0.3 M uridine the red halo was observed only in the case of the rRNA isolated from BrU labeled cells but not from the unlabeled cells.

Figure 4A:
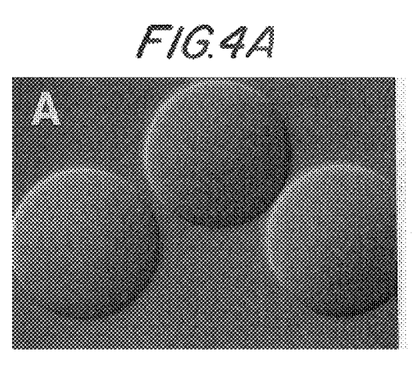
FIG. 4. Binding of halogenated nucleic acids to anti-BrdU coated sepharose (panels A–D) or magnetic (panels E,F) beads.
Figure 4B:
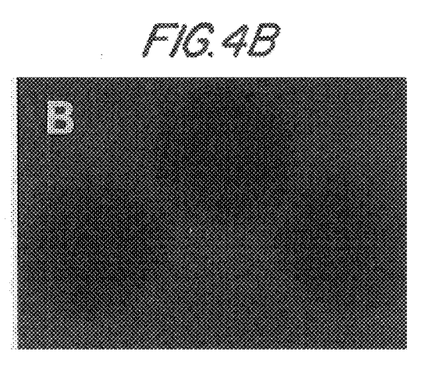
Figure 4C:
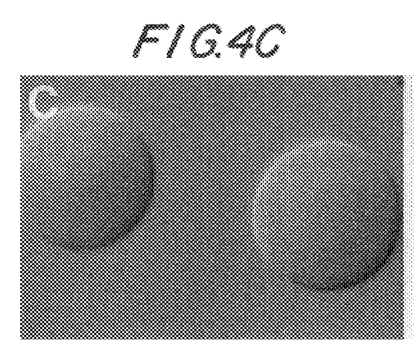
Figure 4D:
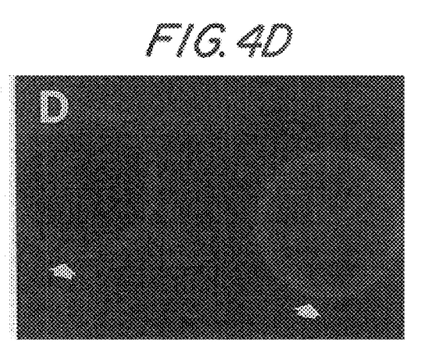
Figure 4E:
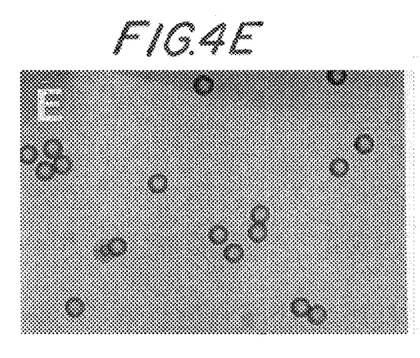
Figure 4F:
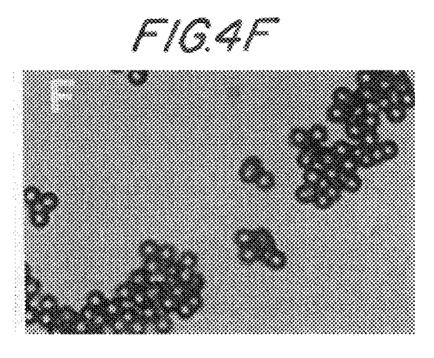

Aggregation of the small (3 μm diameter) magnetic beads was observed (visible to the naked eye as clumps) in the samples containing bromine labeled nucleic acids, most likely reflecting binding of several beads to single chains of the bromine labeled nucleic acids. Under the microscope, large aggregates, most consisting of 4–30 beads were apparent with relatively few (<10%) free single beads (FIG. 4F). Incubation of the aggregated beads with RNase A or DNase I led to rapid dispersion of the respective aggregates. No bead aggregates were observed in the absence of nucleic acids or in the presence of unlabeled DNA or RNA, or with beads that were not coated with the antibody, even if incubated with the labeled nucleic acids: over 90% of the beads were single and the few aggregates observed consisted of a maximum of 5 beads (FIG. 4E).

Significant non-specific binding of the anti-BrdU MoAbs coated beads to unlabeled RNA was also observed similar to the non-specific staining of the filter bound, unlabeled RNA. Likewise in the case of filters, the presence of 0.3 M free uridine abolished aggregation of magnetic beads by the unlabeled RNA but did not prevent aggregation of the beads in the presence of BrU-labeled RNA.

Immunoseparation of BrU-labeled mRNA: In the next experiment the labeled mRNA consisting the transcript of IL1 gene in HL-60 or U937 cells, was recovered by the immunoprecipitation method and analyzed by RT-PCR (FIG. 5). While expression of this gene was minimal in the untreated cells its transcription was induced by phorbol ester treatment for 4 h in the presence of BrU. The labeled nascent mRNA was recovered from the immunoprecipitates by heating the complexes at 80° C. for 10 min in water. The mRNA was then subjected to RT-PCR reaction. The PCR products were detected by EB-agarose gel electrophoresis. The results show that the expected PCR product was detected in the cells in which the gene was induced (FIG. 5A; note the presence of an approximately 0.4 kbp band in PMA induced HL-60 cells). A much lesser amount of product was also detected in the un-induced cells (isolated with anti-BrdU coated meads) suggesting that minor quantity of IL1 mRNA immunoprecipitated from the latter cells. Absence of the PCR product from the induced and the un-induced samples that were immunoprecipitated with uncoated beads confirms the specificity of the immunoseparation technique (FIG. 5B).

BrdU labeling and detection of in vitro synthesized DNA: The labeling and the detection efficiency of DNA synthesized in vitro by different enzymatic systems was assessed in the last set of experiments. First the incorporation of BrdUTP during the RT-PCR reaction was analyzed. The data from several different experiments demonstrated that the dTTP can be partially or totally replaced by BrdUTP without any adverse effects on the reaction, since the product size or the quantity was the same whether the reaction was carried out in the presence of dTTP or BrdUTP (FIG. 6A and C). The products were easily transferred onto a nitrocellulose membrane by routine Southern transfer and detected by normal Western blotting using anti-BrdU antibody (FIG. 6B and D). This suggests that an additional amplification of the PCR signal can be achieved. As seen in FIG. 6A, lane 6, a PCR signal that is barely visible following routine EB staining, shows as a strong thick band, several fold amplified in the immunoblot (FIG. 6B, lane 6). In a second experiment, dTTP was replaced with BrdUTP in the Klenow polymerase mediated DNA synthesis reaction. The products were separated on a gel, transferred onto a nitrocellulose filter and visualized by the immunodetection system (FIG. 6E).

As demonstrated in the above Examples, labeling nucleic acids in vivo with halogenated nucleotides provides great advantages. While the incorporation of biotin or digoxygenin conjugated nucleotides by live cells is limited and these conjugates did not find any significant application in in vivo studies, the halogen tagged nucleotides are easily incorporated into nucleic acids of live cells. Nucleic acids may then be immunochemically detected after cell lysis and nucleic acid extraction. As presently shown, rRNA as well as plasmid DNA, both can be labeled in such a way for their further identification on nitrocellulose filters. Thus, Northern or Southern blots may be detected by immunoblotting thereby providing a combined Northern/Western or Southern/Western approach to nucleic acid analysis. In addition, nucleic acid labelling may be performed in animals or humans. BrdU is frequently administered to cancer patients to assess the proliferative potential of tumors (7, 8).

Even more advantageous than halogen labeling of nucleic acids for their immmunochemical detection, is their selective physical separation. Pulse-labeling with the halogen substituted nucleotide followed by immunoprecipitation of the nucleic acid allows one to selectively separate only that fraction of the nucleic acid which was synthesized during the pulse. The most obvious application of this approach is in the identification of nascent active genes or the genes activated at specific time windows e.g. after induction of cell differentiation, apoptosis, mitogenic stimulation, etc. Immunoprecipitation of pulse-labeled mRNA and their subsequent use in RT PCR reaction provides an opportunity to "fish-out" the genes activated at that time from the pre-existing pool of genes. Likewise, the methodology offers an opportunity to "fish-out" fractions of DNA which undergo the scheduled- or repair- replication at a given time point e.g. after cell's entrance to S phase or induction of DNA damage by radiation or chemical agent. Here again, the possibility of in vivo labeling followed by separation of the labeled nucleic acid species provides an opportunity to analyze gene activation or DNA replication in animals or humans following drug or mutagen administration and may be of value in the clinic.

Antibodies are available which are specific to iodide and chlorine tagged nucleotides which appear not to crossreact with brominated nucleotides (6,20,21). It is potentially possible, therefore, to sequentially pulse label the cells with iodide labeled nucleotides followed by brominated ones (or vice versa) to even more selectively label or separate nucleic acids than is possible with a single label. Messenger RNA separated by such double pulsing, for example, may then be subjected to RT PCR to identify the sequence of activation of particular genes.

REFERENCES

1. Ausubel, F. M., Brent, R., Kingston, R. E., Moore, D. D., Seidman, J. G., Smith, J. A., and Struhl, K. (Eds) (1995) Current Protocols in Molecular Biology, Vols 1–3. John Wiley & Sons, New York.
2. Sambrook, J., Fritsch, E. F., and Maniatis, T. (Eds) (1989) Molecular Cloning. A Laboratory Manual. Second Edition. Cold Spring Harbor Laboratory Press. Cold Spring Harbor, N.Y.
3. Berger, S. L., and Kimmel, A. R., Eds. (1987) Guide to Molecular Cloning Techniques. Meth. Enzymol., Vol. 152. Academic Press, San Diego, Calif.
4. Gratzner, H. G. (1980) Monoclonal antibody to 5-bromo- and 5-iodo-deoxyuridine: a new reagent for detection of DNA replication. (1982) Science, 218: 474–475.
5. Dolbeare F., Gratzner, H., Pallavicini M. G., and Gray, J. W. (1983) Proc. Natl. Acad. Sci. USA 80: 5573–5577.
6. Dolbeare F., and Selden, J. R. (1994) Meth. Cell Biol., 41: 298–316.
7. Begg, A. C., McNally, N. J., Shrieve, D. C., and Karcher, H. (1985) Cytometry, 6: 620–626.
8. Raza, A. G., Miller, M., Mazewski, C., Sheikh, Y., Lampkin, B., Sawaya, R., Crone, K., Berger, T., Reisling J., Gray, J., Khan, S., and Preisler, H. D. (1991) Cell Prolif., 24: 113126.
9. Li, X., Traganos, F., and Darzynkiewicz, Z. (1994) Cancer Res., 54: 4298–4293.

10. Li, X. and Darzynkiewicz, Z. (1995) Cell Prolif., 28: 571–579.
11. Jensen, P. O., Larsen, J., Christiansen, J., and Larsen, J. K., (1993) Cytometry, 14: 455–458.
12. Jensen, P. O., Larsen, J., and Larsen J. K. (1993) Acta Oncol., 32: 521–524, 1993.
13. Li, X., Patel, R., Melamed, M. R., and Darzynkiewicz, Z., (1994) Cell Prolif., 27: 307–319.
14. Leadon, S. A. (1986) Nucleic Acids Res., 14: 8979–8995
15. Sakamoto, H., Traincard, F., Vo-Quang, T., Ternynck, T., Guesdon, J.-L., and Avrameas S. (1987) Mol. Cell. Probes, 1: 109–120.
16. Darzynkiewicz, Z., Traganos, F., Juan, G., and Vibhakar, R. (1996) Physical Separation of Nucleic Acids by Antibodies Towards Halogenated Nucleotides. U.S. patent application No. 60/028,806.
17. Bruno, S., and Darzynkiewicz, Z. (1992) Cell Prolif., 25: 31–40
18. Darzynkiewicz, Z. (1994) In: Cell Biology, A Laboratory Handbook. J. E Celis, Ed. Vol. 1. pp 261–271. Academic Press, San Diego, Calif.
19. Muhlman-Diaz, M. C., Dullea, R. G., Bedford, J. S. (1996) Biotechniques, 21: 82–86.
20. Shibui, S., Hoshino, T., Vanderlaan, M., and Gray, J. (1989) J. Histochem.Cytochem., 37: 1007–1011.
21. Aten J. A., Stap, J., Hoebe, R., Bakker, P. J. M. (1994) Meth. Cell Biol., 41: 317–326.

What is claimed is:

1. A method for labeling RNA by incorporating a 5-position halogenated pyrimidine into the RNA by the steps of: (i) incubating the RNA with 5-position halogenated pyrimidine under conditions whereby the incorporation can occur, (ii) incubating the RNA having incorporated therein a portion of said 5-position halogenated pyrimidine, the incorporated form being a monophosphate pyrimidine, as formed in step (i) with anti-halogenated pyrimidine antibody which binds specifically to said halogenated pyrimidine providing for a means for labeling RNA (iii) separating the labeled RNA from non-labeled RNA.

2. The method of claim 1 wherein said 5-position halogenated pyrimidine is 5-position halogenated uridine triphosphate.

3. The method of claim 1 wherein said 5-position pyrimidine is 5-position brominated uridine.

4. The method of claim 1 wherein said antihalogenated pyrimidine is a labeled antibody.

5. The method of claim 4 wherein the label in said labeled antibody is selected from the group consisting of a fluorochrome label, a peroxidase label, a digoxigen label and a biotin label.

6. The method of claim 1 wherein said antibody is a monoclonal antibody.

7. A method for labeling RNA by incorporating a 5-position halogenated pyrimidine into the RNA by the steps of: (i) incubating the RNA with 5-position halogenated pyrimidine under conditions whereby the incorporation can occur, (ii) incubating the RNA having incorporated therein a portion of said 5-position halogenated pyrimidine, the incorporated form being a monophosphate pyrimidine, as formed in step (i) with anti-halogenated pyrimidine antibody which binds specifically to said halogenated pyrimidine providing for a means of separating such RNA wherein said antibody is bound to a solid support.

8. The method of claim 7 wherein said solid support is a member selected from the group consisting of particles, plates, microspheres, beads, magnetized microspheres and fibers.

9. A method for labeling RNA by incorporating a 5-position halogenated pyrimidine into the RNA by the steps of: (i) incubating the RNA with 5-position halogenated pyrimidine under conditions whereby the incorporation can occur, (ii) incubating the RNA having incorporated therein a portion of said 5-position halogenated pyrimidine, the incorporated form being a monophosphate pyrimidine, as formed in step (i) with anti-halogenated pyrimidine antibody which binds specifically to said halogenated pyrimidine providing for a means of separating such RNA further comprising adding at least one enzyme to step (i) which acts to facilitate the incorporation of said 5-position halogenated pyrimidine into the RNA.

10. A method for isolating RNA which comprises the steps of, (i) incubating the RNA with a 5-position halogenated pyrimidine under conditions whereby the incorporation can occur, (ii) incubating the RNA having incorporated therein a portion of said 5-position halogenated pyrimidine, the incorporated portion being a monophosphate, as formed in step (i) with an antihalogenated pyrimidine antibody which binds specifically to said halogenated pyrimidine and which is attached to a solid support, (iii) isolating said solid support and (iv) separating the RNA from said antibody to isolate the RNA.

11. The method of claim 10 wherein said 5-position halogenated pyrimidine is 5-position halogenated uridine triphosphate.

12. The method of claim 11 wherein said 5-position halogenated pyrimidine is 5-position brominated uridine.

13. The method of claim 11 wherein said antihalogenated pyrimidine is a labeled antibody.

14. The method of claim 13 wherein the label in said labeled antibody is selected from the group consisting of a fluorochrome label, a peroxidase label, a digoxigen label and a biotin label.

15. A method for separating RNA from DNA which comprises the steps of separately incorporating a 5-position halogenated pyrimidine and 5-position halogenated deoxy pyrimidine into the RNA and DNA respectively, by the step of (i) incubating the RNA and DNA with a 5-position halogenated pyrimidine and a 5-position halogenated deoxy pyrimidine under conditions whereby the incorporation of the 5-position halogenated pyrimidine into the RNA and the incorporation of the 5-position halogenated deoxy pyrimidine into the DNA can occur, (ii) incubating the RNA and DNA each having incorporated therein a portion of said 5-position halogenated pyrimidine and said 5-position halogenated deoxy pyrimidine, respectively, the incorporated portion being a monophosphate as formed in step (i), with differently labeled antihalogenated pyrimidine antibodies which bind specifically to said halogenated monophosphate in each case and so as to provide RNA and DNA with different labels and (iii) separating the differently labeled RNA and DNA.

16. A method for separating RNA from DNA which comprises the steps of separately incorporating 5-position halogenated uridine triphosphate and 5-position halogenated deoxyuridine triphosphate into the RNA and DNA respectively, by the step of (i) incubating the RNA and DNA with a 5-position halogenated uridine triphosphate and a 5-position halogenated deoxyuridine triphosphate under conditions whereby the incorporation of the 5-position halogenated uridine triphosphate into the RNA and the incorporation of the 5-position halogenated deoxyuridine triphosphate into the DNA can occur, (ii) incubating the RNA and DNA each having incorporated therein a portion of said 5-position halogenated uridine triphosphate and said 5-position halogenated deoxyuridine triphosphate, respectively, the incorporated portion being a monophosphate as formed in step (i), with differently labeled antihalogenated uridine triphosphate antibodies which bind specifically to said halogenated monophosphate in each case and so as to provide RNA and DNA with different labels and (iii) separating the differently labeled RNA and DNA.

17. The method of claim 15 wherein said 5-position pyrimidine is 5-bromo uridine and said 5-position halogenated, deoxy pyrimidine is 5-bromo deoxyuridine.

18. The method of claim 15 wherein the label for each of said labeled antibodies is a different member selected from the group consisting of fluorochrome, peroxidase, digoxigen and biotin labels.

19. The method of claim 15 wherein said labeled antibodies are each bound to a solid support.

20. The method of claim 19 wherein said solid support is a member selected from the group consisting of particles, plates, microspheres, heads, magnetized microspheres and fibers.

21. The method of claim 15 which comprises adding a least one enzyme to step (i) which acts to facilitate the incorporation of said 5-position halogenated pyrimidine and said 5-position halogenated deoxy pyrimidine into the RNA and DNA respectively.

22. A method for isolating RNA synthesized during a predetermined period of time by the steps of (i) initiating the incubation of said RNA with a 5-position halogenated pyrimidine under conditions whereby said 5-position halogenated pyrimidine is incorporated into said RNA (ii) interrupting said incubation after a predetermined period of time has elapsed, (iii) incubating the RNA having incorporated therein a portion of said 5-position halogenated pyrimidine, the incorporated portion being a monophosphate as formed in step (i) with an antihalogenated pyrimidine antibody which binds specifically to said halogenated monophosphate and (iv) separating said RNA from said antibody to isolate the RNA synthesized during said predetermined period of time.

23. A method for isolating RNA synthesized during a predetermined period of time by the steps of (i) initiating the incubation of said RNA with a 5-position halogenated uridine triphosphate under conditions whereby said 5-position halogenated uridine triphosphate is incorporated into said RNA (ii) interrupting said incubation after a predetermined period of time has elapsed, (iii) incubating the RNA having incorporated therein a portion of said 5-position halogenated uridine triphosphate, the incorporated portion being a monophosphate as formed in step (i) with an antihalogenated pyrimidine antibody which binds specifically to said halogenated monophosphate and (iv) separating said RNA from said antibody to isolate the RNA synthesized during said predetermined period of time.

24. The method of claim 22 wherein said 5-position halogenated pyrimidine is 5-position brominated uridine.

25. The method of claim 22 wherein said antihalogenated pyrimidine is a labeled antibody.

26. The method of claim 25 wherein the label in said labeled antibody is selected from the group consisting of a fluorochrome label, a peroxidase label, a digoxigen label and a biotin label.

27. The method of claim 22 wherein said antibody is bound to a solid support.

28. The method of claim 27 wherein said solid support is a member selected from the group consisting of particles, plates, microspheres, beads, magnetized microspheres and fibers.

29. The method of claim 22 which comprises adding at least one enzyme to step (1) which acts to facilitate the incorporation of said 5-position halogenated pyrimidine into the RNA.

30. A method for labeling RNA for the purpose of its isolation which comprise the steps of (i) incubating a member selected from the group consisting of prokaryotic cells, eukaryotic cells and virus, with a 5-position halogenated pyrimidine under conditions whereby the 5-position halogenated pyrimidine is incorporated into the RNA of said group member, (ii) incubating the RNA having incorporated therein a portion of said 5-position halogenated pyrimidine, the incorporated portion being a monophosphate as formed in step (i) with an antihalogenated pyrimidine antibody which binds specifically to said halogenated monophosphate providing the labeled RNA (iii) separating the labeled RNA from other components.

31. A method of isolating RNA which comprises the steps of (i) incubating a member selected from the group consisting of prokaryotic cells, eukaryotic cells and viruses, with a 5-position halogenated pyrimidine under conditions whereby the 5-position halogenated pyrimidine is incorporated into the RNA of said group member, (ii) incubating the RNA having incorporated therein a portion of said 5-position halogenated pyrimidine, the incorporated portion being a monophosphate as formed in step (i) with an antihalogenated pyrimidine antibody which binds specifically to said halogenated monophosphate and which is attached to a solid support, (iii) isolating said solid support and (iv) separating the RNA from said antibody to isolate the RNA.

32. A method for separating RNA from DNA which comprises the steps of (i) incubating a member selected from the group consisting of prokaryotic cells, eukaryotic cells or viruses with a 5-position halogenated pyrimidine and a 5-position halogenated deoxy pyrimidine into the RNA and DNA respectively under conditions whereby the incorporation of the 5-position halogenated pyrimidine into the RNA and the incorporation of the 5-position halogenated deoxy pyrimidine into the DNA of said group member can occur, (ii) incubating the RNA and DNA each having incorporated therein a portion of said 5-position halogenated pyrimidine and said 5-position halogenated deoxy pyrimidine, respectively, the incorporated portion being a monophosphate as formed in step (i), with differently labeled antihalogenated pyrimidine antibodies which bind specifically to said halogenated monophosphate in each case and so as to provide RNA and DNA with different labels and (iii) separating the differently labeled RNA and DNA.

33. A method for isolating RNA synthesized during a predetermined period of time which comprises the steps of (i) initiating the incubation of a member selected from the group consisting of prokaryotic cells, eukaryotic cells and viruses with a 5-position halogenated pyrimidine under conditions whereby said 5-position halogenated pyrimidine is incorporated into said RNA of said group member, (ii) interrupting said incubation after a predetermined period of time has elapsed, (iii) incubating the RNA having incorporated therein a portion of said 5-position halogenated pyrimidine, the incorporated portion being a monophosphate as formed in step (i) with an antihalogenated pyrimidine antibody which binds specifically to said halogenated monophosphate and (iv) separating said RNA from said antibody to isolate the RNA synthesized during said predetermined period of time.

* * * * *